(12) United States Patent
Goydos et al.

(10) Patent No.: US 7,691,377 B2
(45) Date of Patent: Apr. 6, 2010

(54) METHODS AND COMPOSITIONS FOR TREATING MELANOMA

(75) Inventors: James S. Goydos, East Brunswick, NJ (US); Suzie Chen, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 41 days.

(21) Appl. No.: 11/855,890

(22) Filed: Sep. 14, 2007

(65) Prior Publication Data

US 2008/0124333 A1 May 29, 2008

Related U.S. Application Data

(63) Continuation-in-part of application No. 11/091,076, filed on Mar. 28, 2005, now Pat. No. 7,385,103.

(60) Provisional application No. 60/649,022, filed on Feb. 1, 2005, provisional application No. 60/563,131, filed on Apr. 16, 2004.

(51) Int. Cl.
| | |
|---|---|
| A61K 39/395 | (2006.01) |
| A61K 31/425 | (2006.01) |
| A61K 31/44 | (2006.01) |
| A61K 31/27 | (2006.01) |

(52) U.S. Cl. .................. 424/138.1; 514/367; 514/350; 514/479

(58) Field of Classification Search ............ 424/138.1; 514/367, 350, 479

See application file for complete search history.

(56) References Cited

U.S. PATENT DOCUMENTS

| | | | |
|---|---|---|---|
| 5,869,609 | A | 2/1999 | Mulvihill et al. |
| 6,589,991 | B1 * | 7/2003 | Lai et al. ................... 514/599 |
| 6,923,966 | B2 * | 8/2005 | Rybak et al. ............ 424/195.11 |
| 7,129,073 | B2 * | 10/2006 | Liu et al. ................... 435/194 |
| 7,456,267 | B2 * | 11/2008 | Elson et al. ................. 536/20 |
| 2005/0235366 | A1 | 10/2005 | Chen |

OTHER PUBLICATIONS

Ahmad et al (Proc Am Soc Clin Oncol 22(145):7115, abstract No. 7506, 2004).*
Millward et al (Proc Am Soc Clin Oncol 22(145):7115, abstract No. 7505, 2004).*
Carsons et al (Proc Am Soc Clin Oncol 22:715, abstract No. 2873, 2003).*
Aiba et al., "Reduced Hippocampal Long-Term Potentiation and Context-Specific Deficit in Associative Learning in mGluR1 Mutant Mice", Cell 1994 79:365-375.
Aiba et al., "Deficit Cerebellar Long-Term Depression and Impaired Motor Learning in mGluR1 Mutant Mice", Cell 1994 79:377-388.
Chen et al., "Spontaneous Melanocytosis in Transgenic Mice", J. Invest. Dermatol. 1996 106:1145-1151.
Cohen-Solal et al., "Development of Cutaneous Amelanotic Melanoma in the Absence of a Functional Tyrosinase", Pigment Cell Res 2001 14:466-474.
Colon-Teicher et al., "Genomic Sequences Capable of Committing Mouse and Rat Fibroblasta to Adipogenesis", Nucleic Acids Research 1993 21(9): 2223-2228.
Conquet et al., "Motor Deficit and Impairment of Synaptic Plasticity in Mice Lacking mGluR1", Nature 1994 372:237-243.
Skerry et al., "Glutamate Signalling in Non-Neuronal Tissues", Trends in Pharmacological Sciences 2001 22(4): 174-181.
Zhu et al., "Development of Heritable Melanoma in Transgenic Mice", J. Invest. Dermatol. 1998 110:247-252.
Pollock et al., "Melanoma Mouse Model Implicates Metabotropic Glutamate Signaling in Melanocytic Neoplasia", Nature Genetics, May 2003, 34:1-5.
Marin et al., "Grm5 Expression is Not Required For The Oncogeic Role of Grm1 in Melanocytes", Neuropharmacology, 2005, 49:70-79.
Namkoong et al., "Metabotropic Glutamate Receptor 1 and Gltamate Signaling in Human Melanoma", Cancer Res. 2007; 67L(5), Mar. 1, 2007.
Chen et al., "Aberrant Expression of Metabotropic Glutamate Receptor 1 (GRM1) in Human Melanoma", Melanoma X and The Third Annual International Melanoma Research Congress, Sep. 14-16, 2006; pp. 158-161.
Stepulak et al., "NMDA antagonist inhibits the extracellular signal-regulated kinase pathway and suppresses cancer growth," Proc. Nat'l Acad. Sci. 102(43): 15605-15610, Oct. 25, 2005.

* cited by examiner

*Primary Examiner*—Thaian N Ton
*Assistant Examiner*—Marcia S Noble
(74) *Attorney, Agent, or Firm*—Seed IP Law Group PLLC

(57) ABSTRACT

A method for inhibiting melanoma cell growth in a patient by administering to the patient a therapeutically effective amount of a glutamate release inhibitor, a GRM1 antagonist, or a combination thereof

13 Claims, 5 Drawing Sheets

METHODS AND COMPOSITIONS FOR TREATING MELANOMA

CROSS-REFERENCE TO RELATED APPLICATIONS

This application is a continuation-in-part application of U.S. application Ser. No. 11/091,076, which was filed on Mar. 28, 2005, which claims priority under 35 U.S.C. § 119(e) to U.S. Provisional Application Ser. No. 60/649,022, filed on Feb. 1, 2005 and also claims priority under 35 U.S.C. § 119(e) to U.S. Provisional Application Ser. No. 60/563,131, filed on Apr. 16, 2004. The disclosures of all three applications are incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. RO1CA108720 awarded by the National Institutes of Health and Grant No. ES05022 awarded by the National Institute of Environmental Health Sciences.

BACKGROUND OF THE INVENTION

The incidence of melanoma has been increasing for the past several years. In the United States, more than 60,000 patients are estimated to be diagnosed with melanoma with approximately 8,000 deaths in 2006. The overall lifetime risk of developing melanoma is 1 in 77 for women and 1 in 52 for men.

Melanomas vary greatly in aggressiveness. Very aggressive melanomas grow rapidly, metastasize early, and progress quickly, while less aggressive melanomas grow with a more indolent course. Consequently, much effort has gone into defining the characteristics of the more aggressive melanoma phenotype in hopes of designing therapies that target these more aggressive tumors and sparing patients with less aggressive melanomas often toxic adjuvant therapy designed to lessen the likelihood of recurrence and metastasis.

Metastasis is a multistep process requiring a melanoma cell to escape the control of the local microenvironment and invade the basement membrane. Once in contact with the interstitial microenvironment, integrins on the melanoma cell surface bind to the extracellular matrix (ECM) and this initiates signal transduction events that promote cell survival, migration, and invasion. One signal transduction pathway that appears to be important in melanoma progression is the mitogen activated protein kinase (MAPK) pathway. This signaling pathway begins with Ras activation and proceeds through the activation of Raf and MEK 1/2, resulting in the activation of ERK 1/2. The MAPK pathway controls processes central to melanoma progression, including cell growth, apoptosis, and cell migration. For instance, activation of this pathway leads to upregulation of the expression of proteases such as urokinase-type plasminogen activator (uPA), matrix metalloproteinases (MMP), and tissue plasminagen activator (tPA) that break down the surrounding collagen matrix and promote cell invasion and migration.

Phenotypically aggressive melanoma cells are also very plastic, able to mimic the activities of endothelial cells and to participate in processes such as neovascularization and the formation of fluid-conducting, matrix-rich meshworks. This vasculogenic mimicry has been shown to be a common characteristic of aggressive melanomas and appears to be controlled by complex signal transduction networks within the cell. Indeed, one of the main signaling cascades involved in vasculogenic mimicry is the MAPK pathway, and blocking the phosphorylation of ERK1/2 results in an inhibition of vasculogenic mimicry in three dimensional collagen cultures.

With increased knowledge of the genetic alterations that lead to a more aggressive melanoma phenotype, investigators have been searching for strategies designed to interrupt the relevant signaling pathways and result in either the inhibition of melanoma progression or the preferential killing of melanoma cells. However, different genetic alterations can lead to the activation of the same cellular pathways and inhibiting one pathway component, such as Raf, may not be an effective strategy if other genetic alterations result in downstream target activation. Consequently, we need to continue to work out the relevant signal transduction networks to be able to develop therapies to treat patients with melanoma.

SUMMARY OF THE INVENTION

The present invention provides a method for inhibiting melanoma cell growth in a patient by administering to the patient a therapeutically effective amount of a glutamate release inhibitor, a GRM1 antagonist, or a combination thereof.

In one embodiment, the GRM1 antagonist is a competitive or noncompetitive GRM1 antagonist.

In another embodiment, the glutamate release inhibitor is 2-amino-6-trifluoromethoxybenzothiazole (riluzole).

Optionally, the method further includes administering to the patient an anti-proliferative agent, a chemotherapeutic agent, a B-raf inhibitor, a PI3K inhibitor, an antiapoptosis inhibitor, a benzoquinone ansamycin antibiotic, an antiangiogenesis agent, or a combination thereof.

In one embodiment, the chemotherapeutic agent is selected from 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine [1,1-cyclobutane-dicarboxylato (2-)-0,0']-,(SP-4-2) (carboplatin); and 5β,20-Epoxy-1,2α,4,7β, 10β,13α-hexahydroxytax-11-en-9-one 4,10-diacetate 2-benzoate 13-ester with (2R, 3S)-N-benzoyl-3-phenylisoserine (paclitaxel).

In another embodiment, the B-raf inhibitor is 4-(4-{3-[4-chloro-3-(trifluoromethyl)phenyl]ureido}phenoxy)-N2-methylpyridine-2-carboxamide 4-methylbenzenesulfonate (sorafenib).

In yet another embodiment, the antiapoptosis inhibitor is a Bcl-2 inhibitor.

In another embodiment, the benzoquinone ansamycin antibiotic is geldanamycin or 17-N-allylamino-17-demethoxygeldanamycin.

In yet another embodiment, the antiangiogenesis agent is bevacizumab.

In one embodiment, the glutamate release inhibitor or GRM1 antagonist is administered prior to surgical excision of at least a portion of the melanoma.

In yet another embodiment, the glutamate release inhibitor or GRM1 antagonist is administered following surgical excision of at least a portion of the melanoma.

In one embodiment, the glutamate release inhibitor or GRM1 antagonist is administered in a chronic dose.

In another embodiment, the glutamate release inhibitor or GRM1 antagonist is administered orally, intravenously, or intraperitoneally.

DETAILED DESCRIPTION OF THE INVENTION

Figure 1:
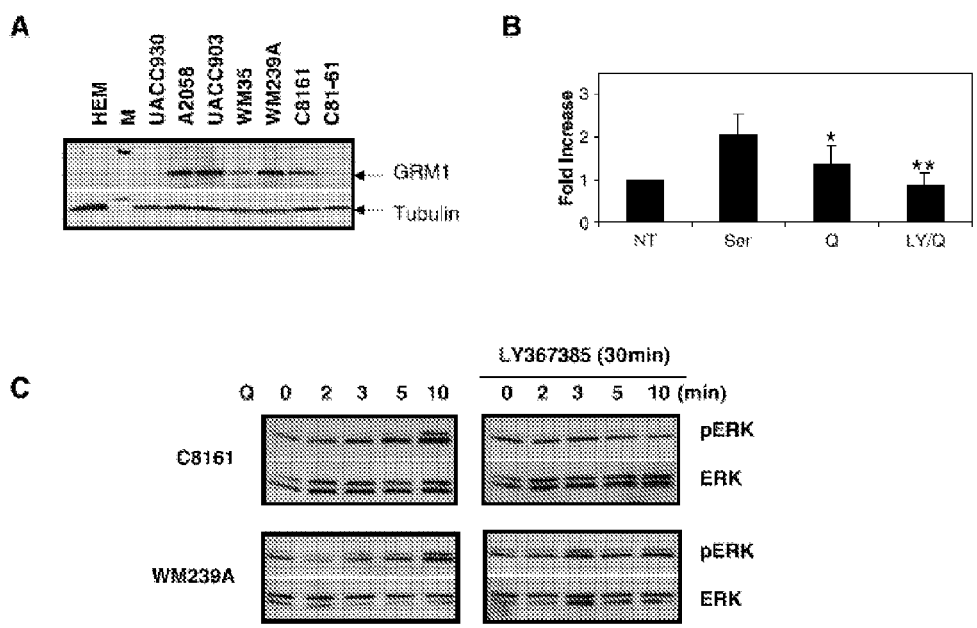
FIG. 1A is an immunoblot for detecting GRM1 protein expression in several human melanoma cell lines.
FIG. 1B is a graph depicting the results of GRM1 agonist-induced IP3 accumulation.
FIG. 1C is an immunoblot demonstrating that stimulation of GRM1 in human melanoma cell lines led to the activation of ERK.

The present invention relates to the discovery of a correlation between the up-regulation of GRM1 and the onset of melanoma. As disclosed in U.S. Publication No. 20050235366, the contents of which are incorporated herein by reference in their entirety, this correlation allows for the development of effective treatments for melanoma by enabling the discovery of novel therapeutic agents that inhibit or antagonize the activities of the GRM1 receptor present in melanoma cells.

Therefore, the present invention provides methods for inhibiting melanoma cell growth in a patient by administering to the patient a therapeutically effective amount of a glutamate release inhibitor, a GRM1 antagonist, or a combination thereof.

The term "melanoma" as used herein includes all types of melanoma, including, for example, melanoma skin cancer, ocular melanoma, and mucosal melanoma.

A preferred glutamate release inhibitor is 2-amino-6-trifluoromethoxybenzothiazole (riluzole).

In one embodiment, the GRM1 antagonist is a competitive or noncompetitive GRM1 antagonist. As used herein the term "competitive antagonist" refers to an antagonist that binds to the same site as the natural ligand glutamate. A preferred competitive antagonist is LY367385. As used herein the term "noncompetitive antagonist" refers to an antagonist that binds to the transmembrane domain of the receptor resulting in stabilization of inactive conformation. A preferred noncompetitive antagonist is BAY36-7620.

Optionally, the composition further includes an anti-proliferative agent, a chemotherapeutic agent, a B-raf inhibitor, a PI3K inhibitor, an antiapoptosis inhibitor, a benzoquinone ansamycin antibiotic, an antiangiogenesis agent, or a combination thereof.

Preferred chemotherapeutic agents include 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine [1,1-cyclobutane-dicarboxylato (2-)-0,0']-,(SP-4-2) (carboplatin); and 5β,20-Epoxy-1,2α,4,7β,10β,13α-hexahydroxytax-11-en-9-one 4,10-diacetate 2-benzoate 13-ester with (2R, 3S)-N-benzoyl-3-phenylisoserine (paclitaxel).

A preferred B-raf inhibitor is 4-(4-{3-[4-chloro-3-(trifluoromethyl)phenyl]ureido}phenoxy) -$N^2$-methylpyridine-2-carboxamide 4-methylbenzenesulfonate (sorafenib).

A preferred antiapoptosis inhibitor is a Bcl-2 inhibitor.

Preferred benzoquinone ansamycin antibiotics include geldanamycin and 17-N-allylamino-17-demethoxygeldanamycin.

A preferred antiangiogenesis agent is bevacizumab.

The term "effective amount" or "therapeutically effective amount" means that amount of a compound or agent that will elicit the biological or medical response of a subject that is being sought by a medical doctor or other clinician.

The glutamate release inhibitor, GRM1 antagonist, and other agents may be administered in a single composition or dosage form or each compound may be independently administered in separate compositions. Separate compositions may be administered simultaneously or sequentially. According to the methods of the present invention, the composition is administered systemically to a patient in need thereof Systemic delivery may be accomplished through, for example, oral or parenteral administration.

More specific routes of administration include intravenous, intramuscular, subcutaneous, intrasynovial, intraperitoneal, transmucosal, and transepithelial including transdermal and sublingual.

For parenteral administration, emulsions, suspensions or solutions of one or more active agents (e.g. glutamate release inhibitor, GRM1 antagonist, anti-proliferative agent, chemotherapeutic agent, B-raf inhibitor, Bcl-2 inhibitor, etc.) in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the glutamate release inhibitor and/or GRM1 antagonist as a free base or pharmacologically acceptable salt can be prepared in water suitably mixed with a surfactant such as hydroxypropyl-cellulose. Dispersions can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating one or more active agents in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

One or more active agents may be also incorporated in a gel or matrix base for application in a patch, which would allow a controlled release of compound through transdermal barrier.

The percentage of one or more active agents in the compositions used in the present invention may be varied, it being necessary that it should constitute a proportion such that a suitable dosage shall be obtained. Several unit dosage forms may be administered at about the same time. A dose employed may be determined by a physician or qualified medical professional, and depends upon the desired therapeutic effect, the route of administration and the duration of the treatment, and the condition of the patient.

The terms "acute dose" or "acute administration" of one or more active agents mean the scheduled administration of the active agent(s) to a patient on an as-needed basis at a dosage level determined by the attending physician to elicit a relatively immediate desired reaction in the patient, given the patient's age and general state of health.

A "sub-acute dose" is a dose of the active agent(s) at a lower level than that determined by the attending physician to be required for an acute dose, as described above. Sub-acute doses may be administered to the patient on an as-needed basis, or in a chronic, or on-going dosing regimen.

The terms "chronic dose" or "continuous administration" of the active agent(s) mean the scheduled administration of the active agent(s) to the patient on an on-going day-to-day basis.

In the adult, the doses are generally from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention. The maximum dosage amount tolerated by the patient is preferred.

The active agent(s) used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active agent(s) may be administered 1 to 4 times per day. Of course, for other patients, it will be necessary to prescribe not more than one or two doses per day.

The glutamate release inhibitor or GRM1 antagonist can be administered during any stage (e.g. early, middle, or advanced) of melanoma. The glutamate release inhibitor or GRM1 antagonist can be administered prior to surgical excision of at least a portion of the melanoma. In another embodiment, the glutamate release inhibitor or GRM1 antagonist is administered following surgical excision of at least a portion of the melanoma. Additionally, the glutamate release inhibitor or GRM1 antagonist can be administered in a chronic dose, for example, following an initial course of therapy.

The following non-limiting examples set forth hereinbelow illustrate certain aspects of the invention.

EXAMPLES

Materials and Methods

Antibodies and reagents. Anti-phosphorylated ERK, anti-ERK, and anti-poly(ADP-ribose) polymerase (PARP) were purchased from Cell Signaling (Danvers, Mass.); GRM1 antibodies were purchased from BD Biosciences (Franklin Lakes, N.J.) and ImmunoStar, Inc. (Hudson, Wis.); and monoclonal α-tubulin antibody, myoinositol, and riluzole were obtained from Sigma (St. Louis, Mo.). DMSO was purchased from Fisher Scientific (Pittsburgh, Pa.). L-quisqualate [(L)-(+)-a-amino-3,5-dioxo-1,2,4-oxadiazolidine-2-propanoic acid] and LY367385 [(S)-(+)-a-amino-4-carboxy-2-methylbenzeneacetic acid] were purchased from Tocris (Ellisville, Mo). BAY36-7620 [(3aS, 6aS)- 6a-naphtalen-2-ylmethyl-5-methyliden-hexahydro-cyclopental[c]-furan-1-on] was obtained from Bayer (West Haven, Conn.).

Cell culture. Primary human epidermal melanocytes (HEM) were purchased from Cascade Biologics (Portland, Oreg.) and maintained in Medium 254 and human melanocyte growth supplements. UACC930, UACC903, and A2058 were provided by Dr. Jeffrey M. Trent (Translational Genomics Research Center, Phoenix, Ariz.). WM239A and WM35 were from Dr. Meenhard Herlyn (Wistar Institute, Philadelphia, Pa.). C8161 and C81-61 were from Dr. Mary J. C. Hendrix (Children's Memorial Research Center, Chicago, Ill.). Melanoma cells were grown in RPMI 1640 plus 10% fetal bovine serum (FBS). For glutamate measurement or induction experiments with GRM1 agonist, to minimize glutamate in the medium, customized glutamine- and glutamate-free RPMI 1640 (Invitrogen-Life Technologies, Carlsbad, Calif.) was used with 10% dialyzed FBS (Invitrogen-Life Technologies) and supplemented with 2 mmol/L GlutaMax (Invitrogen-Life Technologies). For the measurement of inositol-1,4,5-triphosphate (IP3), customized glutamine- and glutamate-free RPMI 1640 was additionally deprived of inositol (Invitrogen-Life Technologies).

Western immunoblots. Protein lysates were prepared as described in K. A. Cohen-Solal et al., "Progressive appearance of pigmentation in amelanotic melanoma lesions," Pigment Cell Res. 15:282-9 (2002). Cells were washed with ice-cold PBS. Extraction buffer was added and cells were collected. After incubation on ice for 20 minutes, supernatants were collected by centrifugation at 4° C. Protein concentration was determined using DC protein assay kit (Bio-Rad, Hercules, Calif.). Routinely, 25 μg of protein lysates were loaded for Western immunoblots.

IP3 measurements. After overnight incubation in the presence of 3 μCi of myo-[$^3$H]inositol (3.22 TBq/mmol; GE Healthcare, Piscataway, N.J.), cells were incubated in fresh glutamate/inositol/serum-free RPMI 1640 with LiCl (10 mmol/L) for 15 minutes in the presence or absence of LY367385 (10 μmol/L) before stimulation with L-quisqualate (10 μmol/L) for 15 min. The reactions were terminated and samples were either washed with the addition of 1 mL of a 1:1 mixture of 1,1,2-trichlorotrifluoroethane (Sigma) and tri-n-octalamine (Sigma) or washed twice with water-saturated diethyl ether (Sigma). Levels of incorporated [$^3$H]inositol in IP3 were measured by a scintillation counter (Beckman Coulter, Inc., Fullerton, Calif.).

DNA transfection. Transfections of DNA were done with N-[1-(2,3-dioleoyloxyl)propyl]-N,N,N,-trimethylammoniummethyl sulfate liposomal transfection reagent (Roche, Basel, Switzerland) according to the manufacturer's instructions. Dominant-negative GRM1 (dnGRM1) constructs were provided by Dr. Anna Francesconi (Albert Einstein College of Medicine, Bronx, N.Y.). DNA transfections were done with 0.5 μg of DNA per 60-mm plate.

3-(4,5-Dimethylthiazol-2-yl)- 2,5-diphenyltetrazolium bromide cell proliferation assays. 3-(4,5-Dimethylthiazol-2-yl)- 2,5-diphenyltetrazolium bromide (MTT) assays were done according to the manufacturer's protocol (Roche). Briefly, $10^3$ cells were plated in 96-well plate and treated with various compounds as indicated. Absorbance was measured by GENios plate reader (Tecan, Durham, N.C.) for the time points indicated.

Measurement of extracellular glutamate. Amplex Red Glutamic Acid/Glutamate Oxidase assay kit (Invitrogen-Molecular Probes) was used to measure the amount of glutamate released in the medium. Cells were grown in medium devoid of glutamate and glutamine but supplemented with GlutaMax (2 mmol/L) for 3 days. Cells were plated at $10^3$ cells per well with 200 μL of medium containing specific compounds with concentration as indicated in 96-well plate. After specified time, 100 μL of medium were collected for measurement of the amount of glutamate released according to the manufacturer's protocol. Cells left with ~100 μL of medium in the wells were used to confirm the viability of cells by MTT cell proliferation assays.

Cell cycle analysis. Cells were plated at $2\times10^6$ per 100-mm culture plate and treated as indicated. After 24 and 48 h, cells were collected and washed twice with ice-cold PBS. Cell pellets were fixed by drop-wise addition of ice-cold 70% ethanol and incubated for 20 minutes at 4° C. Fixed cells were washed twice with ice-cold PBS and resuspended in 500 μL PBS. Cells were treated with RNase A solution (20 μg/mL; Sigma) and labeled with propidium iodide (50 μg/mL; Sigma) for 30 minutes. Cell cycle analysis was done by the Flow Cytometry Facility Core at Rutgers University (Piscataway, N.J.) using a Beckman Coulter system (Epics XL-MCL model).

Xenografts in immunodeficient nude mice. All animal studies were approved by the Institutional Review Board for the Animal Care and Facilities Committee of Rutgers University. Nude mice were purchased from Taconic (Hudson, N.Y.). Human melanoma cells, C8161, were injected into the dorsal area at $10^6$ cells per site. Tumor size was measured twice weekly with a Vernier caliper and calculated as described in A. Stepulak et al., "NMDA antagonist inhibits the extracellular signal-regulated kinase pathway and suppresses cancer growth," Proc. Nat'l Acad. Sci. U.S.A. 102: 15605-10 (2005). Treatment with either vehicle (DMSO) or 7.5 mg/kg riluzole was given daily via p.o. gavage or i.v. when tumor volumes reached 6 mm$^3$. After 18 days of treatment, experiments were terminated due to tumor burden, as tumor volume had reached 300 mm$^3$ in some animals.

Example 1

Functional GRM1 in Human Melanoma Cells

Previous analyses of several human melanoma cell lines and biopsies showed that approximately 40% of them were positive for GRM1 expression. An example of immunoblots of several human melanoma cell lines and normal primary HEMs is shown in FIG. 1A. HEM was used as a normal melanocyte control, and α-tubulin was used as a loading control. Expression of GRM1 was detected in some human melanoma cell lines but not in HEM.

MAPK is one of the key signaling pathways in human melanoma. Therefore, a study was conducted to determine if the MAPK pathway is also critical in GRM1-positive human melanoma cells. It is well known that the common BRAF-activating mutation (V600E) constitutively stimulates MAPK signaling. Therefore, genotypes of BRAF and N-Ras were assessed by DNA sequencing in GRM1-positive human melanoma cell lines. C8161 did not have the most common mutations at either BRAF (codon 600) or N-Ras (codons 12, 13, and 61). However, WM239A displayed a mutation in BRAF (V600D). Most of the other cell lines showed the most common BRAF mutation (V600E; data not shown). In human melanoma cell lines that bore the most common activating mutation in BRAF (V600E), such as UACC903, MAPK pathway was constitutively activated. As a consequence, stimulation with GRM1 agonist did not lead to further activation of ERK (data not shown). Therefore, cell lines bearing the V600E BRAF mutation were excluded from further studies. C8161 and WM239A were selected for subsequent analysis of the involvement of GRM1 signaling in human melanoma.

To examine the functionality of GRM1 in C8161 and WM239A, the cells were stimulated with GRM1 agonist, L-quisqualate (Q), and the accumulation of IP3 was measured (FIG. 1B). The human melanoma cell lines (C8161 and WM239A) were stimulated with L-quisqualate alone (10 μmol/L; Q) for 15 minutes or pretreated with LY367385 (10 μmol/L) for 15 minutes followed by stimulation with L-quisqualate (LY/Q) for 15 minutes. In FIG. 1B, data is expressed relative to no treatments (NT). FBS (10%) was used as a positive control (Ser). Columns represent the average of three independent experiments of a representative cell line (WM239A); bars, SD. *, P<0.05, compared with no treatment (t test); **, P<0.05, compared with L-quisqualate (t test).

Cells were divided into four groups: no treatment, serum as a positive control, treatments with group I mGluR agonist (L-quisqualate), or preincubation with GRM1-specific antagonist, LY367385, followed by induction with L-quisqualate. To minimize the amount of glutamate, the natural ligand of GRM1, glutamate- and glutamine-free media were used for the measurement of IP3 supplemented with GlutaMax. Three independent experiments with C8161 and WM239A human melanoma cell lines were conducted, and representative data are shown. In the presence of serum, an increase in levels of IP3 accumulation was detected when compared with no treatment.

Treatment with GRM1 agonist (L-quisqualate) for 15 minutes resulted in a statistically significant increase in the accumulation of IP3. The specificity of L-quisqualate-induced increase in IP3 accumulation was shown by the absence of IP3 accumulation when these cells were pretreated with GRM1 antagonist (LY367385) followed by induction with L-quisqualate. The functionality of GRM1 in these human melanoma cells was further confirmed by GRM1 agonist-induced ERK phosphorylation (FIG. 1C). L-quisqualate-induced ERK activation was inhibited when these cells were pretreated with LY367385 for 30 minutes before induction with L-quisqualate. Taken together, these results show that GRM1 receptors in these human melanoma cell lines were functional and responded to GRM1 agonist and antagonist.

Example 2

Induction of Apoptosis by dnGRM1

Figure 2:
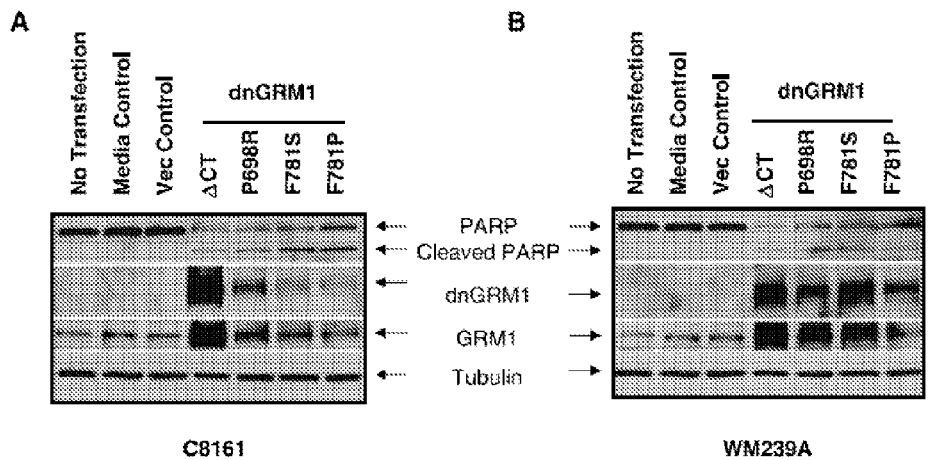
FIGS. 2A and B are immunoblots showing dnGRM1 induced apoptosis in C8161 (A) and WM239A (B)

To further investigate GRM1 functionality and activity in human melanoma cells, two different but complimentary means were used to suppress GRM1 function. First, dnGRM1 was studied. These mutants have a small deletion (DCT 694-695, DCT) or single base substitutions (P698R, F781S, and F781P) in the intracellular loop 2 or 3, which had been shown to be critical in GRM1 signaling. Human melanoma cell lines C8161 (FIG. 2A) and WM239A (FIG. 2B) were transfected with vector control or four different dnGRM1 mutants. At 24 hours after transfection, protein lysates were collected for Western immunoblots. PARP cleavage is a well-known apoptotic marker by the appearance of the cleaved form at 89 kDa. PARP cleavage was detected only in dnGRM1-transfected samples but not in vector control (FIG. 2, top). Second panels show the levels of exogenously transfected GRM1 to verify the presence of dnGRM1 in these cells. dnGRM1 clones were made from a wild-type GRM1 cDNA from rat brain. Therefore, anti-GRM1 antibody that only recognizes the rodent forms of GRM1 was used. Apoptotic marker was only observed in samples that had been transfected with dnGRM1.

Example 3

Inhibition of Human Melanoma Cell Proliferation by GRM1 Antagonists

As a second approach, GRM1 antagonists were used to examine GRM1 functionality and activity in human melanoma cells. LY367385, a competitive antagonist, binds to the same site as the natural ligand glutamate. BAY36-7620, one of the noncompetitive antagonists, binds to the transmembrane domain of the receptor resulting in stabilization of inactive conformation. MTT cell proliferation assay was used to assess growth response of human melanoma cells in the presence of competitive or noncompetitive antagonist.

Figure 3:
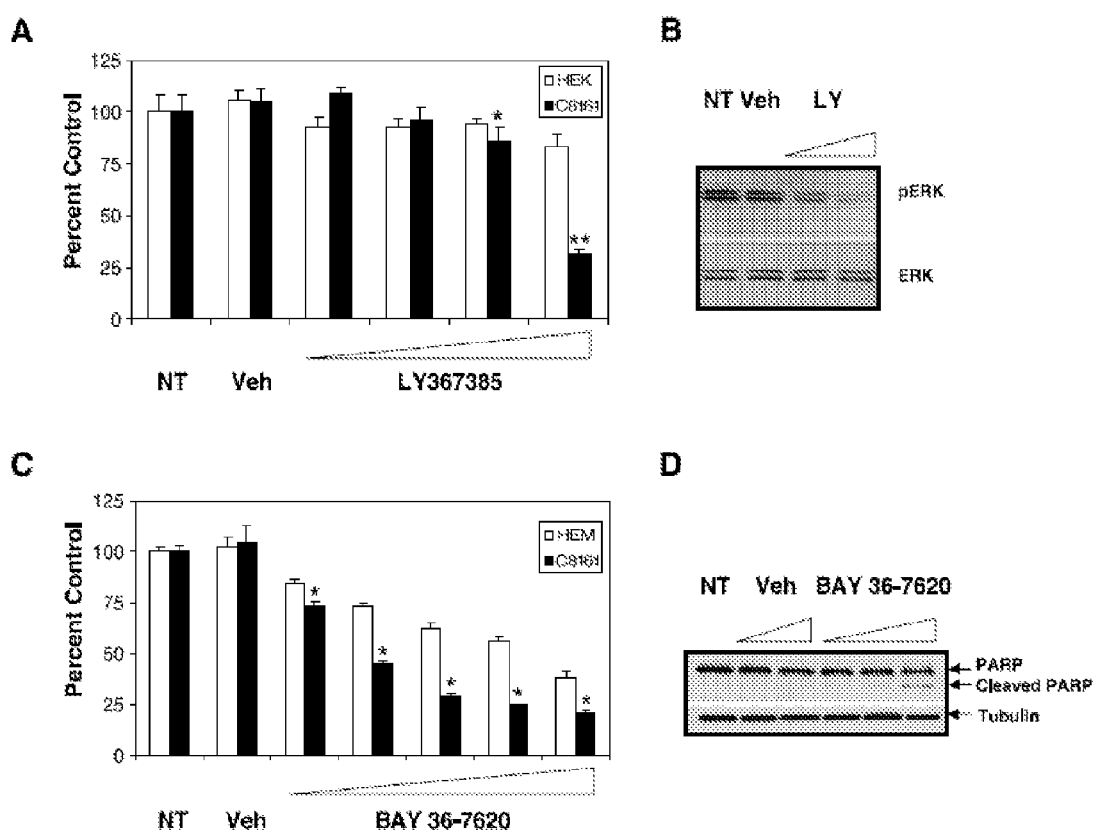
FIG. 3A demonstrates the response of human melanoma cells to LY367385.
FIG. 3B is an immunoblot of ERK phosphorylation after treatments with LY367385 at day 4.
FIG. 3C shows the biological consequences of BAY36-7620 treatments in HEM (white columns) or C8161 (black columns) cells measured by MTT cell viability assays.
FIG. 3D shows Western immunoblots for examining levels of cleaved PARP in C8161 treated with 10, 25, or 50 µmol/L of BAY36-7620 for 48 hours.

Human melanoma cells were grown in the presence of different concentrations of LY367385 in RPMI 1640 devoid of glutamate and glutamine supplemented with GlutaMax because LY367385 competes with the natural ligand glutamate for the binding to GRM1 receptor (FIG. 3A). Cells were treated with LY367385 at concentrations of 10, 50, 100, and 500 µmol/L, respectively. No treatment (NT) and 500 µmol/L NaOH (Veh) were used as controls. Measurement of cell viability/growth was carried out by MTT assays for 4 days. Only measurements on day 4 are shown. Growth of C8161 cells was suppressed in a dose-dependent manner, whereas NaOH virtually had no effect on cell growth (black columns). LY367395 had minimal growth-inhibitory effect on HEK cells (white columns). Bars represent SD. *, P<0.05, compared with HEK (t test); **, P<0.001, compared with HEK (t test).

The growth of primary HEMs requires special medium supplemented with several growth factors, which contain approximately 70 µmol/L glutamate. In the absence of these factors and glutamate, the growth of HEM was inhibited. Therefore, human embryonic kidney (HEK) cells were used as a normal control instead of HEM. Cell proliferation was measured for 4 days, and the growth of C8161 was inhibited by 70% in the presence of 500 µmol/L LY367385. There was only a negligible effect on the growth of HEK cells at this concentration. In a parallel set of cells under same conditions, protein lysates were prepared and levels of phosphorylated ERK were examined (FIG. 3B). C8161 cells were not treated (NT) or treated with 100 or 500 µmol/L of LY367385 or with 500 µmol/L NaOH (Veh). Protein lysates were prepared for Western immunoblots and probed with phosphorylated ERK. The same membranes were stripped and reprobed with total ERK.

A dose-dependent decrease in levels of phosphorylated ERK was detected in cells treated with 100 or 500 µmol/L of LY367385 in comparison with no treatment or vehicle treated. These results showed that treatment of GRM1-positive human melanoma cells with LY367385, a competitive GRM1 antagonist, resulted in suppression in cell proliferation and that this suppression is likely, in part, due to inhibition of MAPK signaling as indicated by a decrease in levels of activated phosphorylated ERK.

Next, the growth of human melanoma cells was examined in the presence of a GRM1 noncompetitive antagonist, BAY36-7620. As a noncompetitive antagonist, BAY36-7620 does not compete for the binding site with the natural ligand glutamate; therefore, regular growth media were used for both human melanoma cells and HEM. MTT cell proliferation assays were done with different concentrations of BAY36-7620 (10-50 µmol/L) for 4 days (only data for day 4 are shown (FIG. 3C)). Bars represent SD; *, P<0.001, compared with HEM (t test). In the presence of BAY36-7620, the growth of C8161 cells was suppressed in a dose-dependent manner, whereas vehicle treatment had very little or no effect on cell growth.

At 30 µmol/L BAY36-7620, only 30% of C8161 cells were viable, whereas >60% of HEM cells were viable. Cell cycle analysis indicated that BAY36-7620-treated C8161 cells showed an increase in the sub-$G_1$ phase after 48 hours of treatment, suggesting an induction of apoptosis by BAY36-7620 (data not shown). Protein lysates were prepared under the same conditions, and PARP cleavage was used as an apoptotic marker. Apoptosis was induced by BAY36-7620 at 50 µmol/L after 48 hours as shown by the cleaved form of PARP in comparison with DMSO treated (Veh) or no treatment (NT) (FIG. 3D). The same blot was probed with α-tubulin to show equal loading.

These data indicated that a noncompetitive antagonist of GRM1, BAY36-7620, inhibited human melanoma cell growth and induced apoptosis, suggesting that GRM1 could be a target in human melanoma therapy.

Example 4

Inhibition of Glutamate Release by GRM1 Antagonists in Human Melanoma Cells

Only 15% inhibition of melanoma cell growth resulted from administration of 100 µmol/L LY367385 in C8161 cells (FIG. 3A), whereas 10 µmol/L LY367385 was sufficient in the suppression of L-quisqualate-induced ERK activation (FIG. 1C). Studies on mouse melanoma cells and mouse melanocytic clones stably expressing GRM1 showed higher levels of released glutamate than normal mouse melanocytes or vector controls. In light of these results, levels of released glutamate by several human melanoma cell lines were examined. Each day, half of the media were collected and the amount of released glutamate was determined. MTT assays were done to ensure that these cells were viable. Again, because HEM, normal human melanocytes, required growth factors as well as glutamate to grow, HEK cells were used as a control. Regardless of whether they express GRM1, all human melanoma cells examined released more glutamate than HEK. In fact, a substantial amount of glutamate was released into the medium, especially by C8161 cells.

Figure 4:
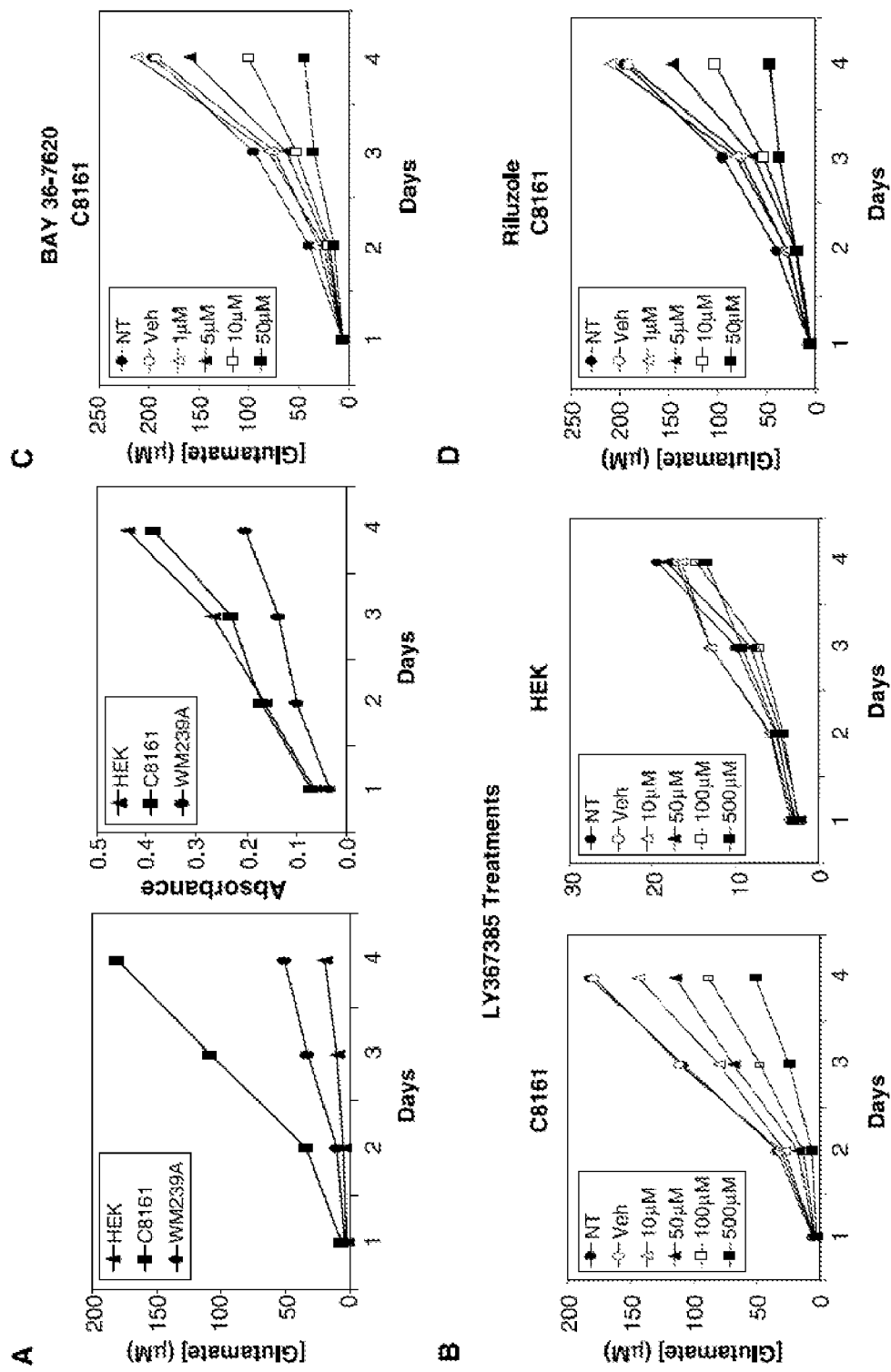
FIG. 4A (left panel) depicts the results of an examination of released glutamate in human melanoma cell lines and HEK cells, and (right panel) depicts MTT cell viability/proliferation assays of a parallel set of cells under the same growth conditions to show the released glutamate was not due to cell death.
FIG. 4B demonstrates the ability of the competitive GRM1 antagonist LY367385 to inhibit the release of glutamate in C8161 and HEK cells at different concentrations for up to 4 days.
FIG. 4C demonstrates that treatment of C8161 cells with BAY36-7620, the noncompetitive GRM1 antagonist, suppressed glutamate release.
FIG. 4D demonstrates that riluzole treatment of C8161 cells suppressed glutamate release.

An example of glutamate released by HEK, C8161, and WM239A is shown (FIG. 4A, left). In FIG. 4A, left, cells were plated in 96-well plates at $10^3$ cells per well and half of the media (100 μL) was collected to measure the amount of glutamate at indicated times. In FIG. 4A, right, cells in the remaining half of the media (100 μL) were proceeded to MTT cell proliferation assays. Media without cells were used as controls in each experiment (data not shown). At least three independent experiments were done. After 4 days, C8161 released approximately 200 μmol/L glutamate into the medium, which was about 10 times the amount released by HEK. Although very little glutamate was released by HEK cells, MTT assay showed their vigorous growth (FIG. 4A, right).

Next, the ability of GRM1 antagonists to inhibit the release of glutamate by these cells was investigated. The vehicle control was 500 μmol/L NaOH. Treatment of C8161 cells with LY367385 resulted in a dose and time-dependent suppression in the levels of released glutamate (FIG. 4B, left). When C8161 cells were treated with 500 μmol/L LY367385, <30% of glutamate was released compared with controls, which correlated with MTT assays. Under the same conditions, very little influence on the glutamate released was detected in LY367385-treated HEK cells (FIG. 4B, right). These results suggested that a higher concentration of LY367385 was required to inhibit GRM1-positive melanoma cell growth due to the constant release of glutamate by these cells. Suppression of glutamate release was also detected in cells treated with BAY36-7620, the noncompetitive GRM1 antagonist (FIG. 4C). DMSO was used as a vehicle control. BAY36-7620 seemed to be more potent in the suppression of glutamate release than LY367385.

Example 5

Inhibition of Cell Proliferation by Glutamate Release Inhibitor Riluzole

Riluzole is a Food and Drug Administration (FDA)-approved drug for amyotrophic lateral sclerosis (ALS; also known as Lou Gehrig's disease). ALS is a degenerative motor neuron disease that gets progressively worse with time. The actual cause of ALS is not known; however, excessive glutamate, a major neurotransmitter, has been proposed to be one of the factors that promotes neuronal excitotoxicity leading to ALS. In clinical trials, the inhibitor of glutamate release, riluzole, is shown to slow down the progression of ALS.

Figure 5:
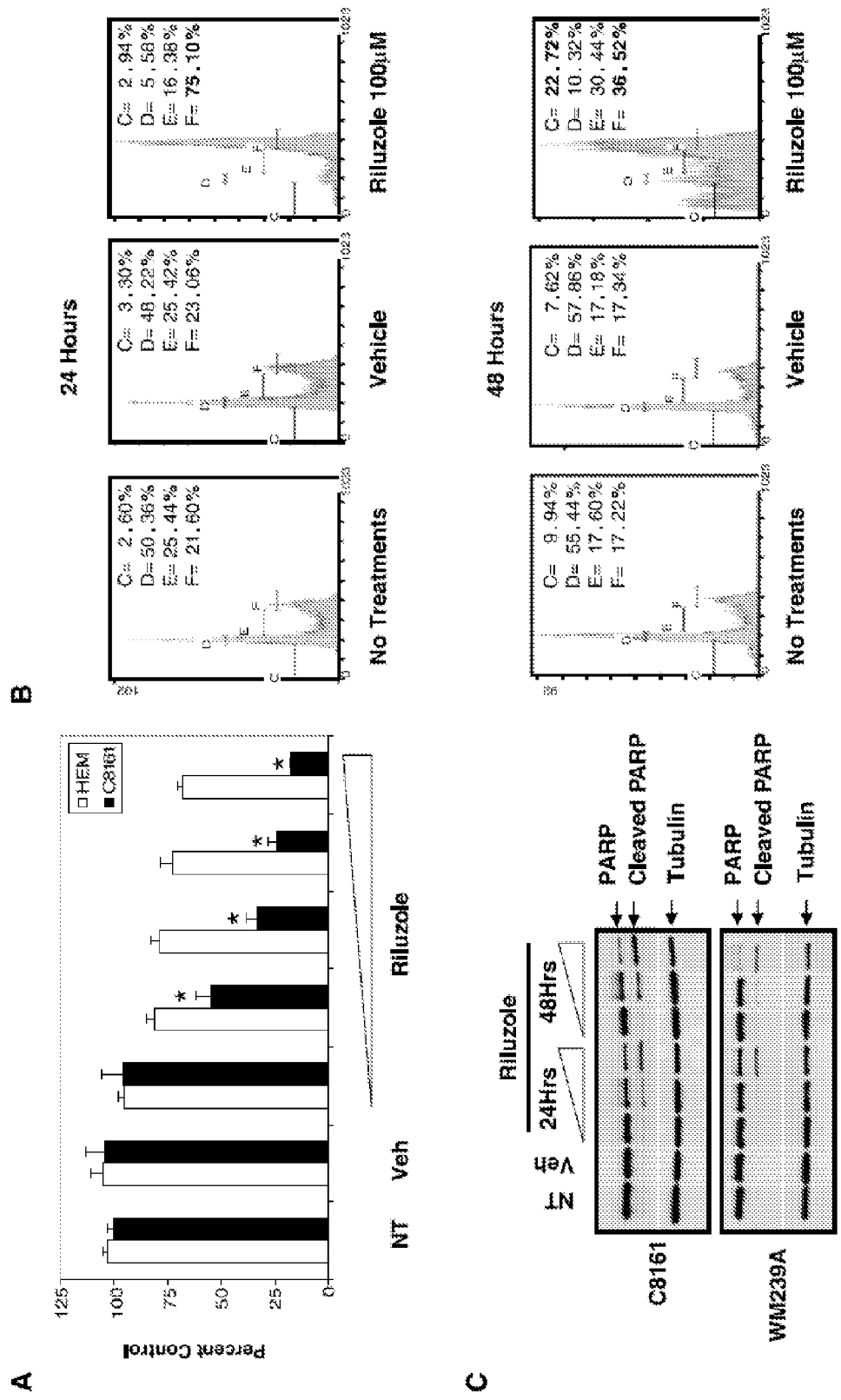
FIG. 5A demonstrates the results of MTT cell proliferation assays used to assess the biological consequences of C8161 (black columns) and HEM (white columns) treated with riluzole.
FIG. 5B demonstrates the results of a cell cycle analysis of C8161 cells treated with riluzole at 24 hours (top) and 48 hours (bottom)
FIG. 5C shows the results of an investigation of the apoptotic response of human melanoma cells to riluzole.

A previous experiment suggested a correlation between levels of released glutamate and cell proliferation (see above). Based on these results, human melanoma cells were treated with riluzole. Riluzole-treated C8161 cells released reduced levels of glutamate (DMSO was used as a vehicle control) (FIG. 4D). Suppression of glutamate release by riluzole also reduced the growth of C8161 human melanoma cells (FIG. 5A). In FIG. 5A, cells were plated on 96-well plate at $10^3$ cells per well and treated with 10, 20, 30, 40, or 50 μmol/L of riluzole. A dose-dependent suppression of C8161 cell growth by riluzole was detected in comparison with no treatment (NT) and DMSO treated (Veh). Only day 4 measurements are shown. Bars represent SD; *, P<0.001, compared with HEM (t test). At 40 μmol/L riluzole, <25% of C8161 cells were viable, whereas >70% of HEM cells were viable, suggesting that HEM cells were less sensitive under similar conditions.

Cell cycle analysis on riluzole-treated C8161 cells showed the accumulation of cells in the $G_2$-M phase at 24 hours (FIG. 5B, top). By 48 hours, there was a substantial increase in cells accumulated in the sub-$G_1$ phase of the cell cycle, suggesting cellular apoptosis (FIG. 5B, bottom). DMSO treatment (Vehicle) had little or no effects. Each phase of cell cycle is indicated as C (sub-$G_1$), D ($G_1$), E (S), and F ($G_2$-M), and the percentage of cells in each phase is given.

To confirm these observations, PARP cleavage was examined by Western immunoblots with C8161 cell lysates prepared at 24 and 48 hours after riluzole treatment (FIG. 5C). Cells were plated and treated with 10, 25, or 50 μmol/L of riluzole for 24 or 48 hours. Protein lysates were extracted for Western immunoblots. After 24 and 48 hours of treatment with 10, 25, and 50 μmol/L of riluzole, cleaved forms of PARP were detected in C8161 compared with no treatment (NT) or DMSO treated (Veh). The same blot was probed with α-tubulin to show equal loading. Results indicated that treatments with riluzole inhibited growth of human melanoma cells and induced cell cycle arrest leading to apoptosis. These results prompted us to validate the antiproliferative, proapoptotic action of riluzole in human melanoma cells in vivo.

Example 6

Inhibition of Human Melanoma Cell Xenograft Growth by Riluzole

Figure 6:
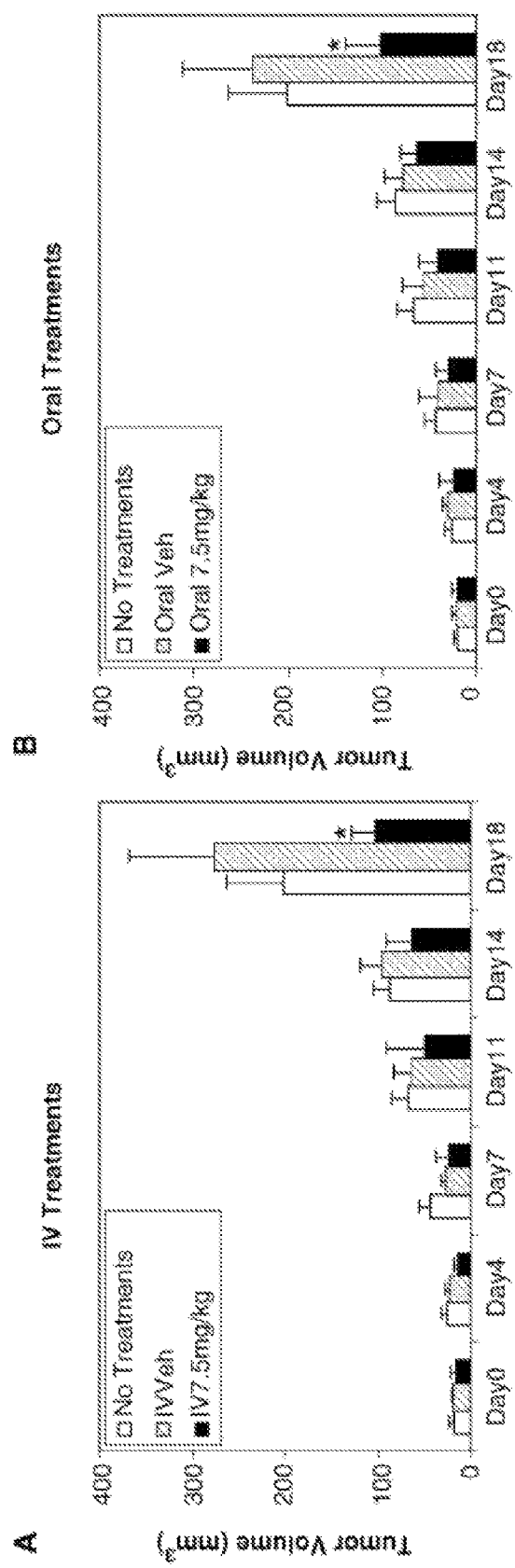
FIGS. 6A and B show the results of an investigation of therapeutic potential of riluzole by C8161 xenograft model.

C8161 cells were inoculated s.c. into nude mice at $10^6$ per site. Based on the experiments done previously by others, the maximum tolerated dose of riluzole was 20 mg/kg. Mice treated with this dose for 2 years had no carcinogenic effects. Based on this information and pilot experiments, mice were treated with 7.5 mg/kg riluzole either by p.o. gavage or i.v. when tumor volume had reached 6 mm³. Mice were treated every day for 18 days, and tumor sizes were measured twice weekly with a Vernier caliper. A significant reduction in tumor volume was observed in mice treated with 7.5 mg/kg riluzole by either i.v. (FIG. 6A) or p.o. gavage (FIG. 6B) compared with untreated or vehicle-treated controls. Bars represent SD; *, P<0.01, compared with untreated and DMSO treated (t test).

Example 7

Phase 0 Trial of Riluzole in Patients with Resectable Stage III and IV Melanoma

Five patients diagnosed with melanomas that expressed Grm1 participated in the trial. Two weeks of therapy with riluzole at 200 mg/day (100 mg every 12 hours) resulted in little toxicity. The only toxic side effect was grade 2 dizziness in two patients. All patients were able to complete the regimen and undergo pre and post treatment biopsy and PET scanning. Four of the five patients has significant decreases in the metabolic activity of their tumors as judged by PET scanning with two patients having a 90% decrease in PET intensity. The same four patients had a statistically significant decrease in the level of activated ERK (by quantitative Western Blotting) in the post treatment specimen as compared to the pre-operative specimen demonstrating a suppression of signaling through the MAPK pathway in these patients. All 5 patients had a decrease in Ki-67 staining in the post-treatment specimen as compared to the pre-treatment specimen demonstrating a decrease in proliferation.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method of inhibiting melanoma cell growth in a patient diagnosed with a melanoma tumor expressing GRM1 comprising administering to said patient an amount of a glutamate release inhibitor, a GRM1 antagonist, or a combination thereof, that is effective to decrease the metabolic activity of said tumor thereby inhibiting melanoma cell growth.

2. The method of claim 1, wherein said GRM1 antagonist is a competitive or noncompetitive GRM1 antagonist.

3. The method of claim 1, wherein said glutamate release inhibitor is 2-amino-6-trifluoromethoxybenzothiazole (riluzole).

4. The method of claim 1, further comprising administering to said patient an anti-proliferative agent, a chemotherapeutic agent, a B-raf inhibitor, a PI3K inhibitor, an antiapoptosis inhibitor, a benzoquinone ansamycin antibiotic, an antiangiogenesis agent, or a combination thereof.

5. The method of claim 4, wherein said chemotherapeutic agent is selected from the group consisting of 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine [1,1-cyclobutane-dicarboxylato (2-)-[0,0']-(SP-4-2) (carboplatin); and 5$\beta$,20-Epoxy-1,2$\alpha$,4,7$\beta$,10$\beta$,13$\alpha$-hexahydroxytax-11-en-9-one 4,10-diacetate 2-benzoate 13-ester with (2R,3S)-N-benzoyl-3-phenylisoserine (paclitaxel).

6. The method of claim 4, wherein said B-raf inhibitor is 4-(4-{3-[4-chloro-3-(trifluoromethyl)phenyl]ureido}phenoxy)-N2-methylpyridine-2-carboxamide 4-methylbenzenesulfonate (sorafenib).

7. The method of claim 4, wherein said antiapoptosis inhibitor is a Bcl-2 inhibitor.

8. The method of claim 4, wherein said benzoquinone ansamycin antibiotic is geldanamycin or 17-N-allylamino-17-demethoxygeldanamycin.

9. The method of claim 4, wherein said antiangiogenesis agent is bevacizumab.

10. The method of claim 1, wherein said glutamate release inhibitor or GRM1 antagonist is administered prior to surgical excision of at least a portion of the melanoma.

11. The method of claim 1, wherein said glutamate release inhibitor or GRM1 antagonist is administered following surgical excision of at least a portion of the melanoma.

12. The method of claim 1, wherein said glutamate release inhibitor or GRM1 antagonist is administered in a chronic dose.

13. The method of claim 1, wherein said glutamate release inhibitor or GRM1 antagonist is administered orally, intravenously, or intraperitoneally.

* * * * *

UNITED STATES PATENT AND TRADEMARK OFFICE
CERTIFICATE OF CORRECTION

PATENT NO. : 7,691,377 B2  Page 1 of 1
APPLICATION NO. : 11/855890
DATED : April 6, 2010
INVENTOR(S) : James S. Goydos et al.

It is certified that error appears in the above-identified patent and that said Letters Patent is hereby corrected as shown below:

Column 14
Claim 5, line 7, "[1,1-cyclobutane-dicarboxylato (2-)-[0,0']-(SP-4-2) (carboplatin);" should read as
--[1,1-cyclobutane-dicarboxylato (2-)-0,0']-(SP-4-2) (carboplatin);--.

Column 14
Claim 6, Line 14, "ureido}phenoxy)-N2-methylpyridine-2-carboxamide" should read as
--ureido}phenoxy)-$N_2$-methylpyridine-2-carboxamide--.

Signed and Sealed this
Twenty-ninth Day of March, 2011

David J. Kappos
*Director of the United States Patent and Trademark Office*